Figure 6:
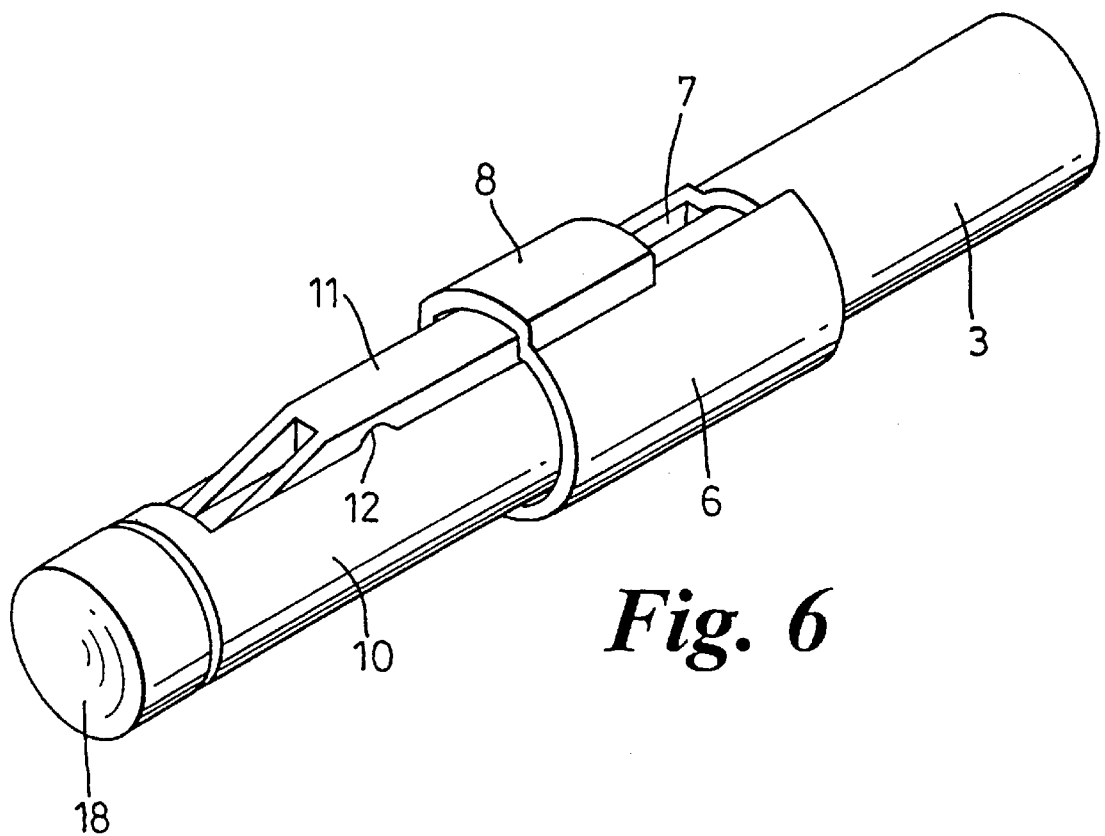

United States Patent
Marshall et al.

[11] Patent Number: 6,077,247
[45] Date of Patent: Jun. 20, 2000

[54] INJECTION DEVICES

[75] Inventors: Jeremy Marshall; David Danvers Crossman, both of Oxford, United Kingdom

[73] Assignee: Owen Mumford Limited, Oxford, United Kingdom

[21] Appl. No.: 09/202,687

[22] PCT Filed: Jun. 16, 1997

[86] PCT No.: PCT/GB97/01614

§ 371 Date: Dec. 18, 1998

§ 102(e) Date: Dec. 18, 1998

[87] PCT Pub. No.: WO97/48430

PCT Pub. Date: Dec. 24, 1997

[30] Foreign Application Priority Data

Jun. 18, 1996 [GB] United Kingdom .................. 9612724

[51] Int. Cl.[7] .............................. A61M 5/20; A61M 5/32; A61M 5/315; A61M 5/00
[52] U.S. Cl. .......................... 604/156; 604/135; 604/192; 604/220; 604/244
[58] Field of Search ................................... 604/191, 192, 604/134–136, 139, 156, 157, 194–196, 218, 220, 232, 244, 264

[56] References Cited

U.S. PATENT DOCUMENTS 5,358,489  10/1994  Wyrick ..................................... 604/136
5,527,287   6/1996  Miskinyar ............................... 604/135

FOREIGN PATENT DOCUMENTS

| 511 524 | 6/1952 | Belgium . |
| 505 931 | 8/1920 | France . |
| 1 014 881 | 8/1952 | France . |
| 2 506 161 | 11/1982 | France . |
| 378 714 | 7/1923 | Germany . |
| 88 13 938 | 1/1990 | Germany . |
| WO 95/19194 | 7/1995 | WIPO . |

*Primary Examiner*—Mark O. Polutta
*Assistant Examiner*—Michael J Hayes
*Attorney, Agent, or Firm*—Young & Thompson

[57] ABSTRACT

An injection device has a two part barrel. The forward part (10) telescopes into the rear part (3) and within the barrel a capsule (1) with a needle (2) at its forward end is initially held by a trigger (11) formed integrally with the forward part (10) so that the needle (2) does not project. The trigger (11) is inoperable at this stage, being inaccessible because of the telescopic overlap. A spring (20) acts on a plunger at the rear of the capsule. When the overlap is increased, the trigger (11) becomes accessible through a slot (7), and when it is operated the capsule (1) is released for the spring (20) to shoot it forwards and eject the dose through the now projecting needle (2). The capsule (1) may have a two part dose and its mixing may then be effected by the spring (20), fully compressed after the overlap increase, urging the plunger forwards.

9 Claims, 3 Drawing Sheets

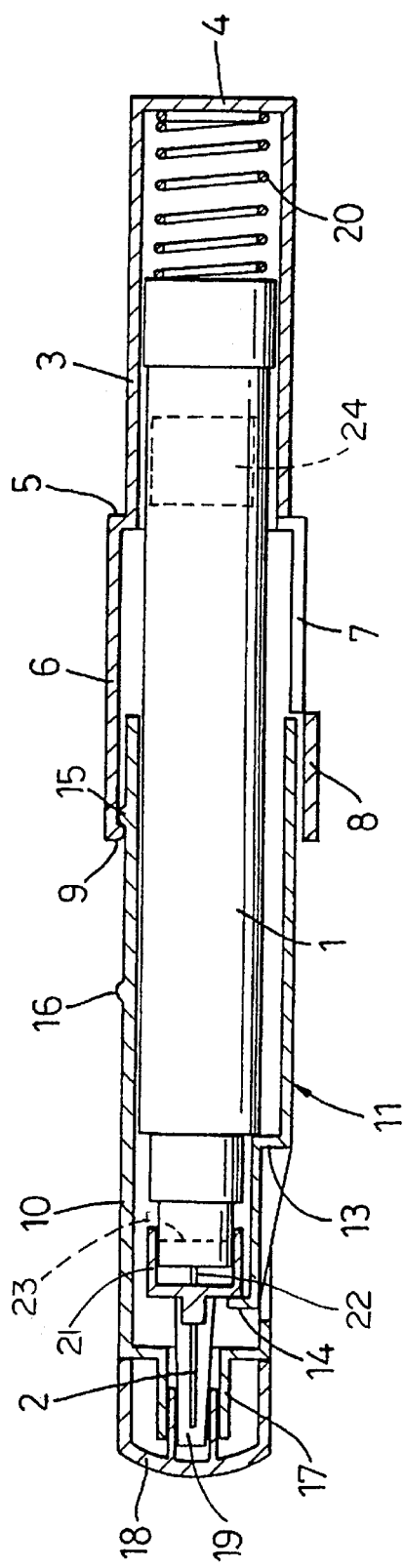
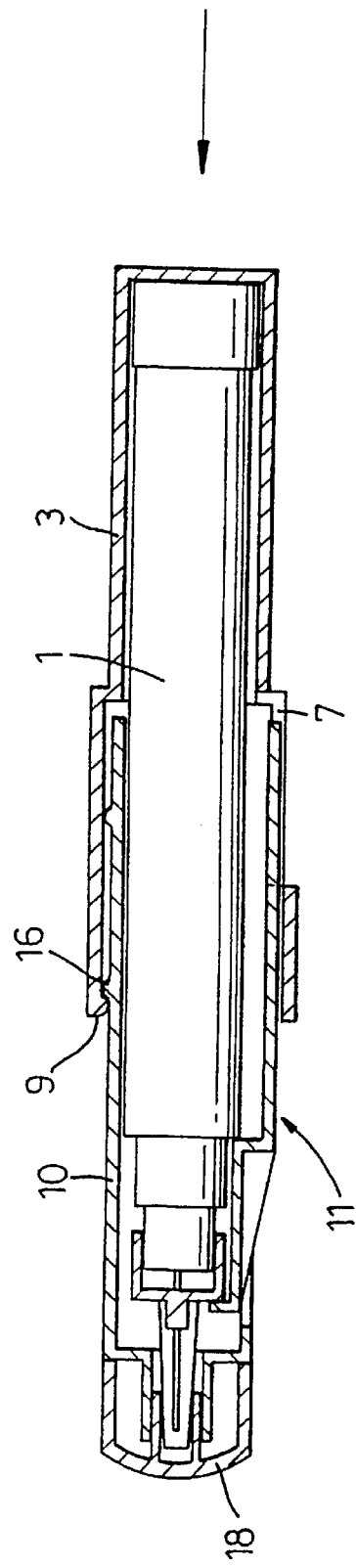
Fig. 1
Fig. 2

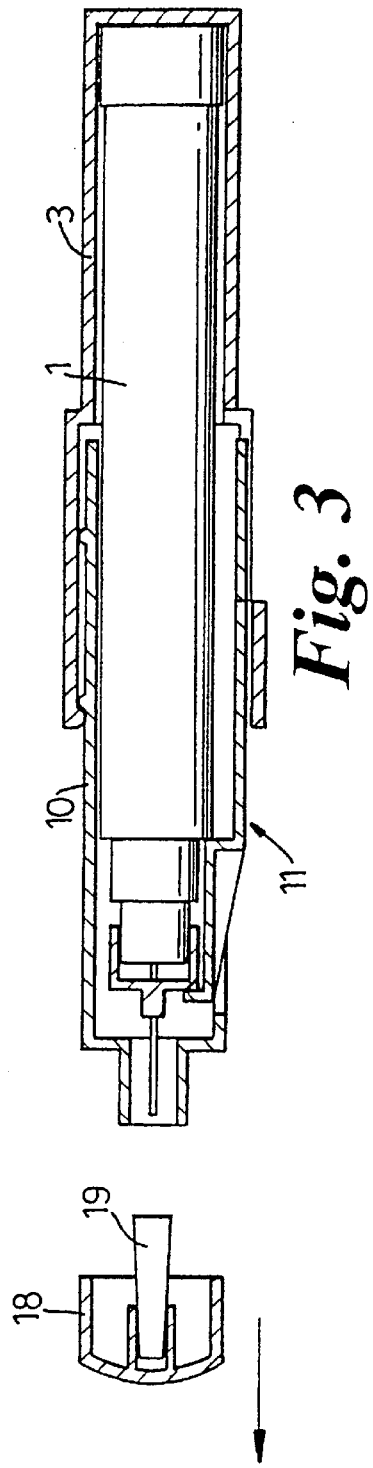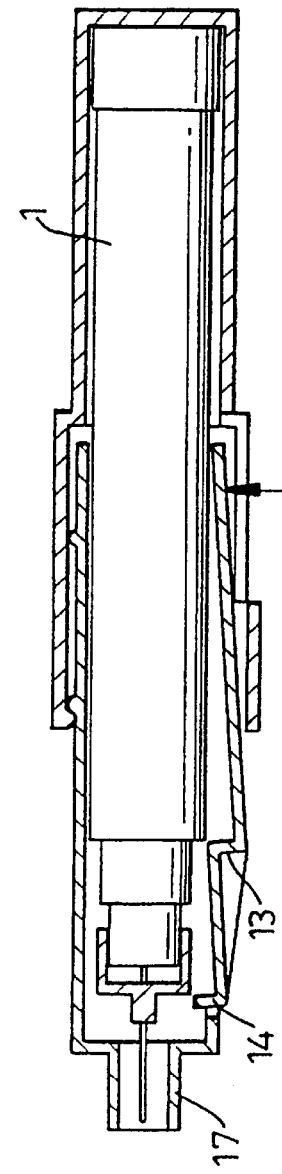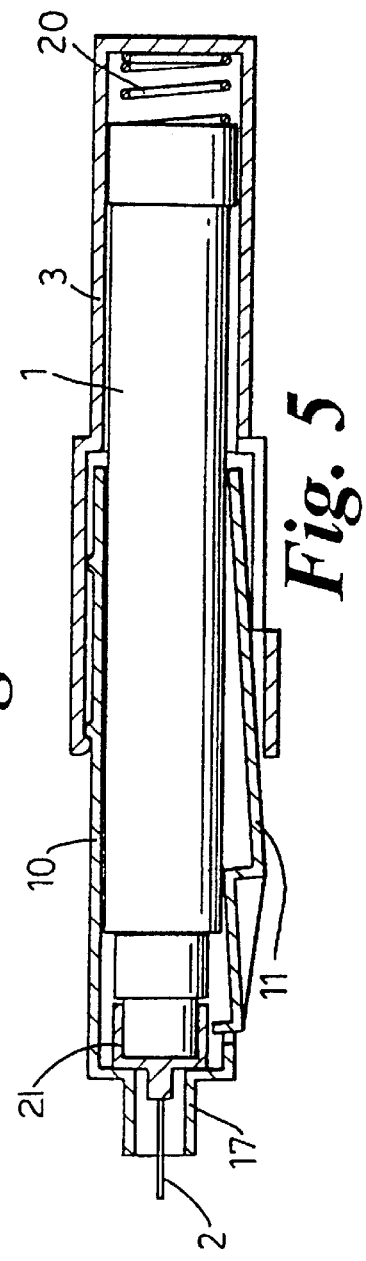

INJECTION DEVICES

This invention relates to injection devices and is particularly but not exclusively concerned with those for capsules where two ingredients are initially separated, but which are mixed immediately prior to injection. These are well known, and will not be described in detail. But a typical arrangement is to have liquid in a rear chamber of the capsule and powder in a forward chamber, the two being connected by a narrow bypass passage. The first stage is to compress the liquid so it forces its way through the bypass gradually to infiltrate and mix with the powder. Then, in the second stage, the plunger is urged forwards and the mixture is injected through the needle at the leading end.

It is the aim of this invention to have a device that will accept such a capsule, with its needle, and operate it, at the same time being of simple construction, with as few parts as possible so that it can be a throwaway item.

According to the present invention there is provided an injector device comprising a two-part barrel, the parts being mutually telescoped and containing spring means to act in a forward direction on a capsule housed therein, the forward part providing a passage at its leading end through which a needle at the leading end of the capsule can be projected, wherein for operation the parts of the barrel have their telescopic overlap increased, which exposes for operation a trigger that holds the capsule in a needle retracted position, actuation of the trigger then releasing the capsule for that to be urged forwardly by the spring means to project the needle.

The spring means may also be arranged, after urging the capsule forwards, to have residual energy to act on the contents of the capsule to eject a dose through the needle.

Conveniently, the forward part of the barrel telescopes into the rearward part.

Preferably the trigger is integrally formed with the part that telescopes into the other one. Generally there will be detents to prevent the parts being detelescoped from either position.

The spring means will conveniently be a coil spring acting between the rear end of the rearward barrel part and the rear end of the capsule.

When the capsule contains two separate components, with a plunger at the rear end of the capsule acted upon by the spring means, the increase in telescopic overlap is conveniently arranged to cause the spring means to be compressed and subsequently re-expand to press the plunger forwards and thereby force one component in the capsule to mix with the other component. The travel of the plunger within the capsule during the mixing operation will preferably be less than the mutual movement of the two barrel parts when the overlap is increased, whereby the spring means will have residual energy after the components have been mixed, first, when the trigger is activated, to shoot the capsule forwards to a limit, acting on the plunger, this projecting the needle, and then to press the plunger further into the capsule and thereby eject a dose through the needle.

With a double-ended needle there can be a lost motion connection between means carrying the needle and the capsule which is taken up during the forward movement of the capsule, causing the rear end of the needle to pierce a membrane defining the forward end of a dose chamber of the capsule.

Figure 7:
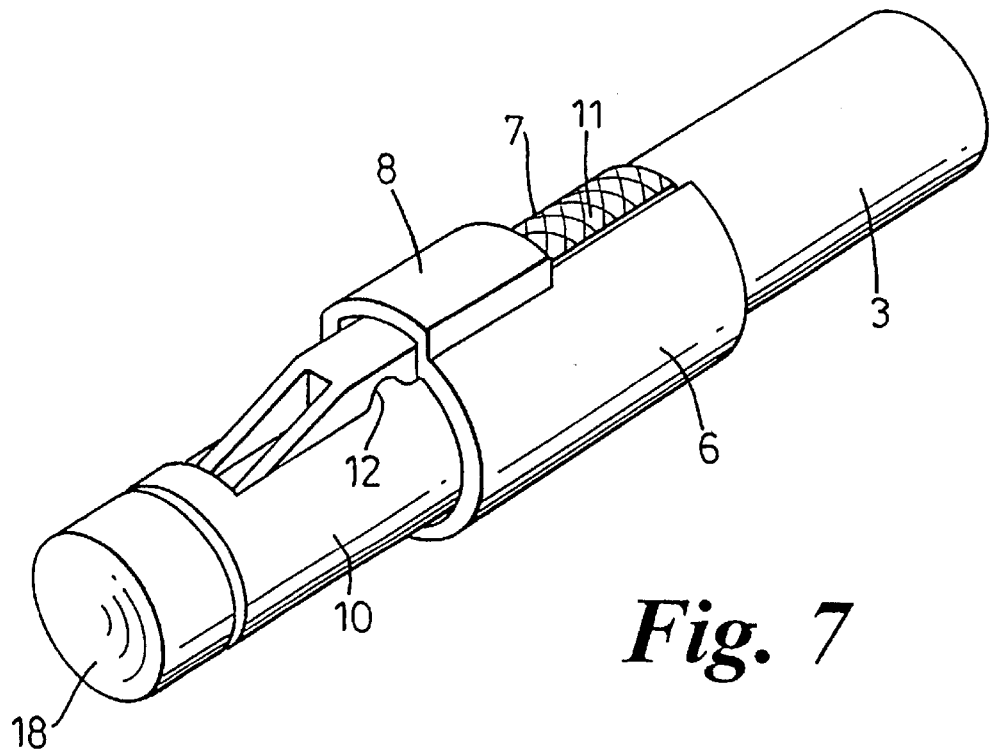

For a better understanding of the invention one embodiment will now be described, by way of example, with reference to the accompanying drawings, in which:

FIGS. 1–5 are axial sections of an injection device in progressive stages of operation, FIG. 6 is a perspective view of the injection device prior to use, and FIG. 7 is a perspective view of the injection device almost ready for use.

The injection device is a two part barrel which contains a capsule 1 with a needle 2 at its leading end. This will have a two component dose which will be mixed and injected during the course of operation. It can be of known type and will not be described in detail.

The rear part 3 of the barrel is of stepped cylindrical form having a closed rear end 4 and a shoulder 5 at about its mid-length where the diameter increases. This enlarged section 6 is not completely cylindrical but has a longitudinal slot 7 extending from the shoulder 5 to an enlargement 8 stepped further out from the section 6. At its forward end, this section 6 has an internal rim 9.

The forward part 10 of the barrel is also generally cylindrical but it has an integral trigger 11. This extends in the longitudinal direction and is joined at its mid-length to the main barrel part 10 by bridging webs 12, as best seen in FIGS. 6 and 7. To the rear of these webs 12, which will serve as pivots being of flexible plastics, the trigger is proud of the part 10 and extends into the enlargement 8 where initially it terminates just short of the slot 7. Forward of its pivot, the trigger steps inwardly at 13 and then continues forwardly to terminate in an inwardly projecting lug 14. The step 13 and the lug 14 bear on a shoulder of the capsule 1 and the forward end of the needle assembly respectively.

Externally, towards the rear end, the part 10 has two circumferential ribs 15 and 16, the rearmost one 15 initially cooperating with the rim 9 to retain the two barrel parts together. At its forward end the barrel part 10 narrows to form a passage 17 through which the needle 2 will be projected, this initially being covered by a cap 18 which plugs into the passage. There, it cooperates with a sheath 19 protecting the leading end of the needle 2. This needle is double ended and is carried by a cup-like member 21 which has a lost motion engagement with the forward end or neck of the capsule 1. Initially, the member 21 is in a forward position in relation to the capsule 1 with the tip of the rear end 22 of the needle adjacent a membrane 23 closing the neck of the capsule 1.

Between a plunger 24 with the rear end of the capsule 1 and the closed end 4 of the part 3 there is a coil spring 20, initially in an expanded, relaxed, condition as shown in FIG. 1. This is the state of the device before use.

For use, the parts 3 and 10 are telescoped further together to the FIG. 2 position where the rim 9 snaps over the rib 16 to retain the parts there. The spring 20 is compressed and initiates the component mixing as described. This further telescoping also exposes the rear end of the trigger 11 in the slot 7.

The cap 18 is then removed as shown in FIG. 3 and this pulls away the sheath 19. The mouth of the passage 17 is then held against the skin and the rear end of the trigger 11 is depressed as shown in FIG. 4. This pivots the trigger so that the step 13 and the lug 14 release the capsule and needle. The spring 20, acting on the plunger 24, therefore shoots the capsule 1 and needle 2 forwards until the needle is arrested by the member 21 meeting the entrance to the passage 17. The capsule 1 continues to move forwards, closing up the lost motion connection as shown in FIG. 5, so that the membrane 23 at its front end is pierced by the rear end 22 of the double ended needle. Then the final expansion of the spring 20 ejects the dose through the needle 2.

The detents formed by the ribs 15 and 16 do allow the rim 9 to snap past them in either direction, so that the barrel can be dismantled and put together again for replacement of a capsule. But of course they are sufficient to stop the two barrel parts simply falling apart.

It will also be understood that, although described in terms of a two-ingredient capsule, the device could work equally well with a single ingredient one that requires no mixing.

What is claimed is:

1. An injection device comprising a barrel (3, 10), spring means (20) within the barrel to act in a forward direction on a capsule (1) with a needle at its leading end housed therein, and a trigger (11) that holds the capsule (1) in a needle retracted position, actuation of the trigger (11) releasing the capsule for that to be urged forwardly by the spring means (20) to project the needle (2) through a passage at the leading end of the barrel (3, 10), characterised in that the trigger (11) has a portion for manual actuation and a portion (12, 14) that co-operates with the capsule, in that the barrel comprises two mutually telescoped parts (3, 10) one of which initially conceals said actuating portion, and in that, for operation, those parts have their telescopic overlap increased to energise the spring means (20) and to expose said portion for manual actuation.

2. An injection device as claimed in claim 1, characterised in that the spring means (20) are arranged, after urging the capsule (1) forwards, to have residual energy to act on the contents of the capsule to eject a dose through the needle (2).

3. An injection device as claimed in claim 1, characterised in that said forward part (10) telescopes into the rearward part (3).

4. An injection device as claimed in claim 1, characterised in that the trigger (11) is integrally formed with the part (10) that telescopes into the other part (3).

5. An injection device as claimed in claim 1, characterised in that there are detents (9, 15, 16) to resist the parts being detelescoped from the initial position and from the increased overlap position.

6. An injection device as claimed in claim 1, characterised in that the spring means (20) is a coil spring acting between the rear end (4) of the rearward barrel part (3) and the rear end of the capsule (1).

7. An injection device as claimed in claim 1, in combination with a capsule (1) containing two initially separate components, characterised in that a plunger at the rear end of the capsule is acted upon by the spring means (20), the increase in telescopic overlap causing the spring means to be compressed and subsequently re-expand to press the plunger forwards and thereby force one component in the capsule to mix with the other component.

8. An injection device as claimed in claim 7, characterized in that the spring means (20) are arranged, after urging the capsule (1) forwards, to have residual energy to act on the contents of the capsule to elect a dose through the needle (2) and that the travel of the plunger within the capsule during the mixing operation is less than the mutual movement of the two barrel parts when the overlap is increased, whereby the spring means (20) has residual energy after the components have been mixed, first, when the trigger is activated, to shoot the capsule (1) forwards to a limit, acting on the plunger, this projecting the needle (2), and then to press the plunger further into the capsule and thereby eject a dose through the needle (2).

9. An injection device as claimed in claim 1, in combination with a capsule, characterised in that the needle (2) is double-ended and there is a lost motion connection between means carrying the needle and the capsule (1) which is taken up during the forward movement of the capsule, causing the rear end of the needle to pierce a membrane defining the forward end of a dose chamber of the capsule.

\* \* \* \* \*